United States Patent
Thundat et al.

(10) Patent No.: US 7,243,548 B2
(45) Date of Patent: Jul. 17, 2007

(54) SURFACE WAVE CHEMICAL DETECTOR USING OPTICAL RADIATION

(75) Inventors: Thomas G. Thundat, Knoxville, TN (US); Robert J. Warmack, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 149 days.

(21) Appl. No.: 11/100,839

(22) Filed: Apr. 7, 2005

(65) Prior Publication Data

US 2005/0223806 A1 Oct. 13, 2005

Related U.S. Application Data

(60) Provisional application No. 60/560,135, filed on Apr. 7, 2004.

(51) Int. Cl.
 *G01N 30/00* (2006.01)
 *B01D 15/04* (2006.01)
(52) U.S. Cl. .............................. 73/590; 73/597; 73/602; 73/24.02
(58) Field of Classification Search .................. 73/590, 73/649, 602, 592, 597, 24.01, 24.06, 31.06, 73/30.04, 32 A, 328; 356/328; 422/82.05, 422/82.02, 82.09
See application file for complete search history.

(56) References Cited

U.S. PATENT DOCUMENTS

| | | | |
|---|---|---|---|
| 4,457,162 A * | 7/1984 | Rush et al. | ................. 73/24.01 |
| 5,291,422 A * | 3/1994 | Esztergar | ..................... 702/30 |
| 5,923,421 A | 7/1999 | Rajic et al. | |
| 6,180,415 B1 | 1/2001 | Schultz et al. | |
| 6,321,588 B1 * | 11/2001 | Bowers et al. | ............. 73/24.01 |
| 6,331,276 B1 | 12/2001 | Takei et al. | |
| 6,408,681 B1 * | 6/2002 | Gurton et al. | ............. 73/24.02 |
| 6,486,476 B1 * | 11/2002 | Ochiai et al. | .......... 250/370.01 |
| 6,515,749 B2 | 2/2003 | Pipino | |
| 6,684,683 B2 * | 2/2004 | Potyrailo et al. | .......... 73/24.06 |
| 6,974,524 B1 * | 12/2005 | Jaso et al. | ............. 204/192.13 |
| 7,102,132 B2 * | 9/2006 | Ludviksson | ................. 250/343 |
| 2007/0041870 A1 * | 2/2007 | Yamanaka et al. | ............ 422/58 |

* cited by examiner

*Primary Examiner*—Hezron Williams
*Assistant Examiner*—Jacques Saint Surin
(74) *Attorney, Agent, or Firm*—Kirk A. Wilson

(57) ABSTRACT

A surface wave chemical detector comprising at least one surface wave substrate, each of said substrates having a surface wave and at least one measurable surface wave parameter; means for exposing said surface wave substrate to an unknown sample of at least one chemical to be analyzed, said substrate adsorbing said at least one chemical to be sensed if present in said sample; a source of radiation for radiating said surface wave substrate with different wavelengths of said radiation, said surface wave parameter being changed by said adsorbing; and means for recording signals representative of said surface wave parameter of each of said surface wave substrates responsive to said radiation of said different wavelengths, measurable changes of said parameter due to adsorbing said chemical defining a unique signature of a detected chemical.

22 Claims, 1 Drawing Sheet

SURFACE WAVE CHEMICAL DETECTOR USING OPTICAL RADIATION

CROSS-REFERENCE TO RELATED APPLICATIONS

This application claims priority to U.S. Provisional Patent Application 60/560,135 filed Apr. 7, 2004, and is herein incorporated by reference.

STATEMENT REGARDING FEDERALLY SPONSORED RESEARCH

This invention was made with United States Government support under Contract No. DE-AC05-00OR22725 between the United States Department of Energy and U.T. Battelle, LLC. The United States Government has certain rights in this invention.

BACKGROUND OF THE INVENTION

It is well established that surfaces can support mechanical waves. Depending on the nature of the substrate, these surface waves are called Rayleigh waves, Lamb waves, and Love waves. Rayleigh waves are for thicker substrates while Lamb and Love waves are for thin membranes. The surface waves can be generated on a piezoelectric substrate using electrode arrays deposited on the surface. Once created, the wave travels on the surface and can be detected using a second electrode array. If the surface waves encounter adsorbed species, the frequency of the wave varies very sensitively due to mass or stress loading. The frequency of the wave can be very high—hundreds of MHz—yet the frequency and phase can be measured very precisely to obtain extremely high sensitivity.

One important disadvantage of the above surface-wave sensor is its inability to distinguish between different chemical species. This disadvantage also exists on other mass sensors such as the quartz crystal microbalance (QCM), plate wave resonator, and Lamb and Love wave sensors. To overcome this disadvantage of lack of chemical selectivity, SAW sensors are generally coated with a chemically selective layer. However, this chemically selective layer frequently does not provide good chemical selectivity except in rare cases, for example, biosensors based on antibody-antigen interaction or DNA hybridization. Polymeric coatings are used in certain vapor sensors and are sensitive to a variety of analytes depending upon the solubility of the analyte in each polymer. To provide unambiguous detection of even a single analyte in a mixture that may contain other analyte vapors, for example, arrays of sensors with various polymers are required to provide even qualitative information about the nature of the adsorbates and thus the vapors.

Surface waves can also be extremely sensitive to temperature, depending upon the nature of the piezoelectric substrate. With appropriate material, small changes in temperature can cause rather large changes in frequency, wave velocity, and phase. In this invention, we exploit this extremely high sensitivity of surface waves to temperature and other physical properties to achieve chemical selectivity using photo-absorption. In addition to temperature, the surface wave velocity is affected by pressure, surface stress, magnetic and electric fields. This invention exploits changes in surface wave velocity due to variation in surface temperature, pressure, surface stress, electric and magnetic field induced by interaction of adsorbate with impinging electromagnetic radiation on the sensor surface. A variation in surface acoustic wave properties such as frequency, velocity, phase, amplitude, and Q-factor as a function of the wavelength of the impinging electromagnetic wave is used as a signatures for speciation of adsorbed species.

U.S. Pat. No. 6,180,415 to Schultz et al.; U.S. Pat. No. 6,331,276 to Takei et al.; and U.S. Pat. No. 6,515,749 to Pipino teach sensor devices and methods using only optical parameter changes for detection. U.S. Pat. No. 5,923,421 to Rajic et al., herein incorporate by reference teaches similar absorption spectrometry devices and methods using bolometers, thermopiles, pyroelectrics or microcantilever sensing elements.

BRIEF DESCRIPTION OF THE INVENTION

A surface wave chemical detector comprising at least one surface wave substrate, each of said substrates having a surface wave and at least one measurable surface wave parameter; means for exposing said surface wave substrate to an unknown sample of at least one chemical to be analyzed, said substrate adsorbing said at least one chemical to be sensed if present in said sample; a source of a radiation for respectively radiating and thereby heating said surface wave substrate with different wavelengths of said monochromatic spectrum, said surface wave parameter being changed by said adsorbing; and means for recording signals representative of said surface wave parameter of each of said surface wave substrates responsive to said radiation of said different wavelengths, measurable changes of said parameter due to adsorbing said chemical defining a unique signature of a detected chemical.

This invention gains chemical selectivity by exposing the surface with adsorbed chemical species (adsorbate) to certain wavelengths that are indicative of the species present. High sensitivity of surface waves is combined with chemical selectivity of absorption spectroscopy. This approach does not necessarily depend upon coatings, thus greatly improving selectivity and avoiding the long-standing issues related to degradation of external coatings.

DETAILED DESCRIPTION OF THE INVENTION

Figure 1:
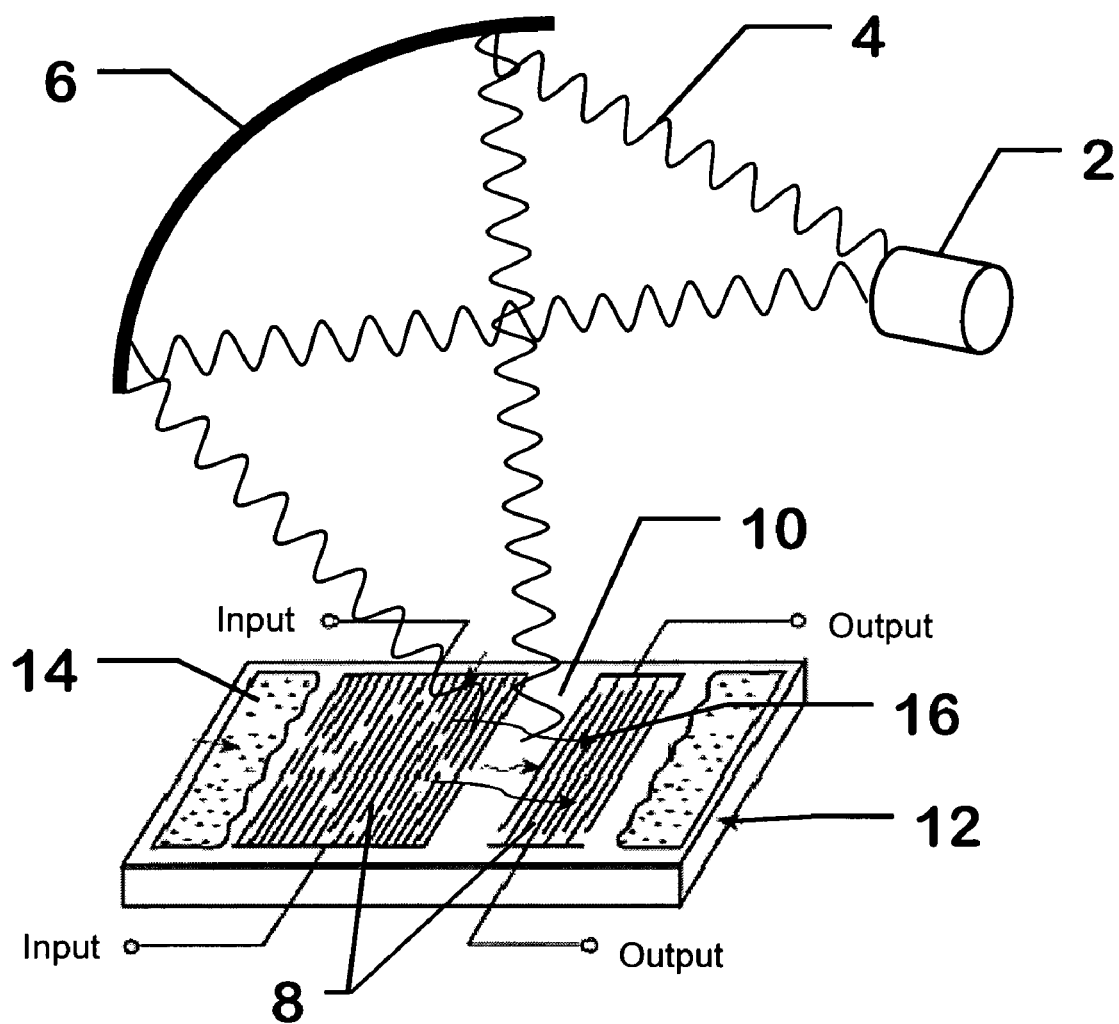
FIG. 1 is an embodiment of the surface wave detector using biasing electrodes on a piezoelectric substrate.

An apparatus and method is taught that combines the extreme high sensitivity of surface wave sensors with high selectivity of absorption spectroscopy producing chemically selective surface wave sensors.

Chemical analytes adsorb at certain frequencies of electromagnetic radiation. Absorption spectroscopy is a standard technique used to identify and quantify chemical species, for example, Fourier-transform infrared spectroscopy. This invention combines the high sensitivity of surface waves to small changes in temperature and other physical properties with optical spectroscopy for the adsorbed species. As the adsorbed molecules absorb electromagnetic radiation corresponding to some unique electronic, vibration or rotational transition, they excite by re-emission or transfer energy into translational mode. This relaxation process increases the surface temperature of the substrate. Since the surface waves are extremely sensitive to temperature, the frequency variation of the surface waves follows the absorption spectra of the particular adsorbed molecules. Other effects include optical-induced stress changes, mass changes due to desorbing molecules, acoustic impedance, density, etc. Additionally, the mass change due to the adsorbed species can also be measured at a reference lighting condition—for example, no light—to gain additional information about the nature of the adsorbed species (for example, amount, presence of additional materials, etc.).

In addition to temperature, the surface wave velocity is affected by pressure, surface stress, magnetic and electric fields. This invention exploits changes in surface wave velocity due to variation in surface temperature, pressure, surface stress, electric and magnetic field induced by interaction of adsorbate with impinging electromagnetic radiation on the sensor surface. A variation in surface acoustic wave properties such as frequency, velocity, phase, amplitude, and Q-factor as a function of the wavelength of the impinging electromagnetic wave is used as a signatures for speciation of adsorbed species.

The surface can be uncoated presenting the native surface to the absorbing species or can be treated to present a more favorable surface for the absorbing species. Such surface treatments can include monolayers assembled onto the surface that can make the surface polar or non-polar, such as is used in chromatographic columns. The treatment can also include a film of material that may be porous or permeable to the absorbing species. Such coating can be used to concentrate the analytes of interest by their partition function, thus increasing the sensitivity of the device. Again, the native surface may be satisfactory for many analytes of interest.

It is well known that molecular adsorption on a SAW surface changes the surface acoustic wave properties. In this invention we expose the adsorbed species to electromagnetic waves where the adsorbate molecules absorb the electromagnetic waves creating localized changes in surface temperature which in turn affect the properties of the surface acoustic waves. The variation in surface wave properties as a function of illuminating wavelength has the unique chemical signature of the adsorbate where the adsorbed species absorb the electromagnetic waves. The surface acoustic wave properties can be frequency, velocity, phase, acoustic impedance and Q-factor. In addition to absorption spectrum of the adsorbates, other physical and chemical properties of the adsorbates can be exploited for obtaining chemical signatures of the adsorbed species. For example, illumination with UV light can induce triplet states or free radicals in certain chemicals producing localized variation in electric and magnetic field intensity which in turn affect the surface acoustic wave properties.

The present invention has a number of embodiments. All the embodiments utilize surface waves. The surface waves can be of different types. The sample surface is illuminated using radiation such as a pulsed light source. Scanning the wavelength allows determination of wavelengths that are absorbed by the sample.

Embodiment I (FIG. 1): In this embodiment, the analyte (gas or liquid) is taken into a chamber containing the surface acoustic wave (SAW) or other device with a temperature-dependent surface wave (Lamb wave, Love wave, etc.) In this embodiment, interdigitated arrays 8 excite surface waves 16 coupled to adsorbed species 14 on a piezoelectric substrate 12. The surface waves are modulated by pulsed radiation 4, such as light, that is directed using a focusing system 6 onto the substrate 12. The radiation 4 comes from a radiation source 2 with wavelengths chosen to allow selectivity for the analytes of interest. Optical absorption by analytes absorbed upon or near the surface wave cause heating and other effects upon the surface, which in turn affect the frequency and other characteristics of the device such as frequency, velocity, and phase. The surface may be coated to concentrate analytes on each sensor. Such coatings can be selected from a set of self-assembled monolayers, polymers, sol-gels. The sensor may also be left uncoated in cases where condensation of an analyte would occur on the surface. The readout is enhanced considerably by modulating or chopping the light beam and synchronously demodulating the resultant signal. Scanning the wavelength of the light by means of a monochromator or selecting alternate wavelengths by using active or passive filters can permit the determination of several analytes or interferences. An alternate embodiment would array several detectors, each with its own filter, to make a simple array sensor.

Embodiment II: In this embodiment, a thin micromachined membrane is excited by a light source or by electromagnetic induction to create surface waves on the membrane. For example, a micromachined thin-film widow is pulsed with a high intensity focused light source that is localized in size. The sudden change in temperature produces a wave that travels away from the source. The wave can be detected with a high frequency cantilever placed on the membrane, by optical deflection, or by capacitive readout or built-in piezoresistive or piezoelectric readout. Such readout methods are well known. Such a device would be coated (or not) and be exposed to selected wavelengths as described above to obtain chemical selectivity and specificity.

Embodiment III (FIG. 1): In this embodiment the surface waves 16 are created by focused pulsed radiation 4 on a piezoelectric substrate 12. The wavelength of the light is such that it can produce electron-hole pairs in the substrate 12. The substrate 12 can be a non-centro-symmetric crystal such as ZnO or GaAs. The surface inherently has a band bending. The light creates charge carriers that reach the localized illumination spot on the surface because of band bending. The charge then spreads out. An annular or lateral electrode placed around or near the illumination spot can detect the electronic waves created by the pulsed light. The presence of adsorbed species 14 on the surface can change the surface wave 16 velocity and other characteristics. Although such variations are sufficient to detect analytes, this method gives little chemical specificity. Again, chemical identification can be obtained by exposing the adsorbed molecules to optical radiation with wavelengths characteristic of the adsorbates.

Embodiment IV: The fourth embodiment, also shown in FIG. 1, varies from the Embodiment III in one critical way. In this embodiment, a depletion layer 10 is created below the adsorbed species 14 using interdigitated arrays 8 such as biasing electrodes on a substrate 12, such as a piezoelectric Si as used in a SAW, and is illuminated with various frequencies using a radiation source 2 such as a monochromator and a focusing system 6 such as a mirror to accumulate charges. Generally a highly doped semiconductor substrate is preferred. The semiconductor is biased to in such a way that depletion is formed at the surface (interface). This may be done using electrodes directly attached to the semiconductor, similar to a photocell or may be in an electrochemical environment, in which an electrode is coupled to the surface through an electrolyte.

Illumination at energies above band gap produces electron-hole pairs that are separated by electric field in the depletion layer. The bias and semiconductor dopant can be selected in such a way that either electrons or holes will come to the surface. The collection of electrons or holes at the surface forms a two dimensional pool of charge carriers. Surface waves in the two dimensional pool of charge carriers are created by pulsing a focused light on the surface as in Embodiment III or by means of an electrode (generator) placed on the surface. Another electrode (detector) placed around or nearby the first electrode serves as the pickup. In the case of electrode wave generation, a pulsed or modulating voltage applied to the generator electrode to create charge waves rides on the top of the constant bias used for creating the depletion layer.

The invention has been described in terms of specific embodiments which are indicative of a broad utility but are not limitations to the scope of the invention. Additions and modifications apparent to those with skill in the art are included within the scope and spirit of the invention.

We claim:

1. A surface wave chemical detector, comprising:
   at least one surface wave substrate, each of said substrates having a surface wave propagation at a frequency and at least one measurable surface wave parameter;
   means for exposing said surface wave substrate to an unknown sample of at least one chemical to be analyzed, said substrate adsorbing said at least one chemical to be sensed if present in said sample;
   a source of radiation for radiating said surface wave substrate with different wavelengths of said radiation, said surface wave parameter being changed by said adsorbing; and,
   means for recording signals representative of said surface wave parameter of each of said surface wave substrates responsive to said radiation of said different wavelengths, measurable changes of said surface wave parameter due to adsorbing said chemical defining a unique signature of a detected chemical.

2. The detector of claim 1 wherein said surface wave is at least one selected from the group consisting of Rayleigh waves, Lamb waves, and Love waves.

3. The detector of claim 1 wherein said surface wave parameter is at least one selected from the group consisting of velocity, phase, amplitude, and Q-factor.

4. The detector of claim 1 wherein said means for recording signals further comprises absorption spectroscopy to identify and quantify said chemical.

5. The detector of claim 1 wherein said means for recording signals further comprises a mass change determination of adsorbed chemicals.

6. The detector of claim 1 wherein said at least one substrate further comprises at least one coating for preferentially adsorbing different chemicals.

7. The detector of claim 6 wherein said coating is at least one coating selected from the group consisting of self-assembled monolayers, polymers, sol-gels, chemically specific porous material, and chemically specific permeable material.

8. The detector of claim 1 wherein said surface wave substrate is at least one substrate selected from the group consisting of thin micromachined membrane, piezoelectric material, non-centro-symmetric crystal, and semiconductor material.

9. The detector of claim 8 wherein said semiconductor substrate further comprises a depletion layer created using biasing electrodes.

10. The detector of claim 1 wherein said source of radiation is selected from at least one of the group consisting of a light source from a monochromator, a light source with at least one filter set, and a laser.

11. The detector of claim 1, wherein said at least one surface wave substrate is disposed in an array.

12. A method for detecting chemicals, comprising the steps of:
   preferentially adsorbing at least one chemical to be sensed onto at least one surface wave substrate having a measurable surface wave parameter, said substrate propagating a surface wave at a frequency;
   measurably changing said surface wave parameter by exposing said substrate to an unknown sample of at least one chemical to be analyzed;
   radiating said adsorbed chemical by radiating said substrate with different wavelengths from a source of radiation;
   measuring said changing of said surface wave parameter due to said adsorbing; and
   defining a unique signature of a detected chemical with said measurable changes of said surface wave parameter.

13. The method of claim 12 wherein said surface wave is at least one selected from the group consisting of Rayleigh waves, Lamb waves, and Love waves.

14. The method of claim 12 wherein said surface wave parameter is at least one selected from the group consisting of velocity, phase, amplitude, and Q-factor.

15. The method of claim 12 wherein said defining step further comprises absorption spectroscopy to identify and quantify said chemical.

16. The method of claim 12 wherein said defining step further comprises a mass change determination of adsorbed chemicals.

17. The method of claim 12 wherein said at least one substrate further comprises at least one coating for preferentially adsorbing different chemicals.

18. The method of claim 17 wherein said coating is at least one coating selected from the group consisting of self-assembled monolayers, polymers, sol-gels, chemically specific porous material, and chemically specific permeable material.

19. The method of claim 12 wherein said surface wave substrate is at least one substrate selected from the group consisting of thin micromachined membrane, piezoelectric material, non-centro-symmetric crystal, and semiconductor material.

20. The method of claim 19 wherein said semiconductor substrate further comprises a depletion layer created using biasing electrodes.

21. The method of claim 12 wherein said source of radiation is generated using at least one selected from the group consisting of a light source using a monochromator, a light source using at least one filter set, and a laser.

22. The method of claim 12, wherein said at least one surface wave substrate is disposed in an array.

* * * * *